United States Patent
Oppelaar

(10) Patent No.: US 8,912,402 B2
(45) Date of Patent: Dec. 16, 2014

(54) BEAN VARIETY RX 08081162

(75) Inventor: Arie Oppelaar, Ijzendoorn (NL)

(73) Assignee: Seminis Vegetable Seeds, Inc., Woodland, CA (US)

( * ) Notice: Subject to any disclaimer, the term of this patent is extended or adjusted under 35 U.S.C. 154(b) by 324 days.

(21) Appl. No.: 13/473,486

(22) Filed: May 16, 2012

(65) Prior Publication Data

US 2013/0232634 A1 Sep. 5, 2013

Related U.S. Application Data

(60) Provisional application No. 61/605,955, filed on Mar. 2, 2012.

(51) Int. Cl.
- *A01H 5/00* (2006.01)
- *A01H 5/10* (2006.01)
- *A01H 1/00* (2006.01)
- *C12N 15/82* (2006.01)

(52) U.S. Cl.
USPC ........... 800/313; 800/260; 800/268; 800/278; 435/421; 435/430

(58) Field of Classification Search
None
See application file for complete search history.

(56) References Cited

U.S. PATENT DOCUMENTS 8,173,877 B2 * 5/2012 Gehin ........................... 800/298

OTHER PUBLICATIONS

Moose SP, Mumm RH., "Molecular plant breeding as the foundation for 21st century crop improvement", *Plant Physiol.*; 147(3):969-77; Jul. 2008.

Variety specific information as indicated in transmittal letter of Apr. 16, 2013 Information Disclosure Statement for U.S. Appl. No. 13/473,486.

* cited by examiner

*Primary Examiner* — Stuart F Baum

(74) *Attorney, Agent, or Firm* — Dentons US LLP; Alissa Eagle, Esq.

(57) ABSTRACT

The invention provides seed and plants of the bean line designated RX 08081162. The invention thus relates to the plants, seeds and tissue cultures of bean line RX 08081162, and to methods for producing a bean plant produced by crossing a plant of bean line RX 08081162 with itself or with another bean plant, such as a plant of another line. The invention further relates to seeds and plants produced by such crossing. The invention further relates to parts of a plant of bean line RX 08081162, including the pods and gametes of such plants.

22 Claims, No Drawings

BEAN VARIETY RX 08081162

CROSS-REFERENCE TO RELATED APPLICATIONS

This application claims the priority of U.S. Provisional Appl. Ser. No. 61/605,955, filed Mar. 2, 2012, the entire disclosure of which is incorporated herein by reference.

FIELD OF THE INVENTION

The present invention relates to the field of plant breeding and, more specifically, to the development of bean line RX 08081162.

BACKGROUND OF THE INVENTION

The goal of crop breeding is to combine various desirable traits in a single variety/hybrid. Such desirable traits may include greater yield, resistance to insects or pests, tolerance to heat and drought, better agronomic quality, higher nutritional value, growth rate and fruit or pod properties.

Breeding techniques take advantage of a plant's method of pollination. There are two general methods of pollination: a plant self-pollinates if pollen from one flower is transferred to the same or another flower of the same plant or plant variety. A plant cross-pollinates if pollen comes to it from a flower of a different plant variety.

Plants that have been self-pollinated and selected for type over many generations become homozygous at almost all gene loci and produce a uniform population of true breeding progeny, a homozygous plant. A cross between two such homozygous plants of different varieties produces a uniform population of hybrid plants that are heterozygous for many gene loci. Conversely, a cross of two plants each heterozygous at a number of loci produces a population of hybrid plants that differ genetically and are not uniform. The resulting non-uniformity makes performance unpredictable.

The development of uniform varieties requires the development of homozygous inbred plants, the crossing of these inbred plants, and the evaluation of the crosses. Pedigree breeding and recurrent selection are examples of breeding methods that have been used to develop inbred plants from breeding populations. Those breeding methods combine the genetic backgrounds from two or more plants or various other broad-based sources into breeding pools from which new lines are developed by selfing and selection of desired phenotypes. The new lines are evaluated to determine which of those have commercial potential.

One crop species which has been subject to such breeding programs and is of particular value is garden bean (*Phaseolus vulgaris* (snap)). Beans are annual, warm-season legumes. Garden beans, also known as green beans, snap beans, or pole beans, are grown primarily for their pods, which are harvested for consumption in their succulent form, whereas dry beans (*Phaseolus vulgaris* (dry)), lima beans (*Phaseolus limensis*), and soybeans (*Glycine max*) are usually grown for the seed itself. In addition, the bean leaf is occasionally used as a leaf vegetable, and the straw is used for fodder.

SUMMARY OF THE INVENTION

In one aspect, the present invention provides a bean plant of the bean line designated RX 08081162. Also provided are bean plants having all the physiological and morphological characteristics of bean line RX 08081162. Parts of the bean plant of the present invention are also provided, for example, including pollen, an ovule, a pod, and a cell of the plant.

The invention also concerns seed of bean line RX 08081162. The bean seed of the invention may be provided as an essentially homogeneous population of bean seed of the line designated RX 08081162. Essentially homogeneous populations of seed are generally free from substantial numbers of other seed. Therefore, in one embodiment, seed of line RX 08081162 may be defined as forming at least about 97% of the total seed, including at least about 98%, 99%, or more of the seed. The population of bean seed may be particularly defined as being essentially free from hybrid seed. The seed population may be separately grown to provide an essentially homogeneous population of bean plants designated RX 08081162.

In another aspect of the invention, a plant of bean line RX 08081162 comprising an added heritable trait is provided. The heritable trait may comprise a genetic locus that is, for example, a dominant or recessive allele. In one embodiment of the invention, a plant of bean line RX 08081162 is defined as comprising a single locus conversion. In specific embodiments of the invention, an added genetic locus confers one or more traits such as, for example, herbicide tolerance, insect resistance, disease resistance, and modified carbohydrate metabolism. In further embodiments, the trait may be conferred by a naturally occurring gene introduced into the genome of the line by backcrossing, a natural or induced mutation, or a transgene introduced through genetic transformation techniques into the plant or a progenitor of any previous generation thereof. When introduced through transformation, a genetic locus may comprise one or more genes integrated at a single chromosomal location.

In another aspect of the invention, a tissue culture of regenerable cells of a plant of line RX 08081162 is provided. The tissue culture will preferably be capable of regenerating plants capable of expressing all of the physiological and morphological characteristics of the line, and of regenerating plants having substantially the same genotype as other plants of the line. Examples of some of the physiological and morphological characteristics of the line RX 08081162 include those traits set forth in the tables herein. The regenerable cells in such tissue cultures may be derived, for example, from embryos, meristems, cotyledons, pollen, leaves, anthers, roots, root tips, pistil, flower, seed and stalks. Still further, the present invention provides bean plants regenerated from a tissue culture of the invention, the plants having all the physiological and morphological characteristics of line RX 08081162.

In yet another aspect of the invention, processes are provided for producing bean seeds, plants and pods, which processes generally comprise crossing a first parent bean plant with a second parent bean plant, wherein at least one of the first or second parent bean plants is a plant of the line designated RX 08081162. These processes may be further exemplified as processes for preparing hybrid bean seed or plants, wherein a first bean plant is crossed with a second bean plant of a different, distinct line to provide a hybrid that has, as one of its parents, the bean plant line RX 08081162. In these processes, crossing will result in the production of seed. The seed production occurs regardless of whether the seed is collected or not.

In one embodiment of the invention, the first step in "crossing" comprises planting seeds of a first and second parent bean plant, often in proximity so that pollination will occur for example, mediated by insect vectors. Alternatively, pollen can be transferred manually. Where the plant is self-pollinated, pollination may occur without the need for direct human intervention other than plant cultivation.

A second step may comprise cultivating or growing the seeds of first and second parent bean plants into plants that bear flowers. A third step may comprise preventing self-pollination of the plants, such as by emasculating the male portions of flowers, (i.e., treating or manipulating the flowers to produce an emasculated parent bean plant).

A fourth step for a hybrid cross may comprise cross-pollination between the first and second parent bean plants. Yet another step comprises harvesting the seeds from at least one of the parent bean plants. The harvested seed can be grown to produce a bean plant or hybrid bean plant.

The present invention also provides the bean seeds and plants produced by a process that comprises crossing a first parent bean plant with a second parent bean plant, wherein at least one of the first or second parent bean plants is a plant of the line designated RX 08081162. In one embodiment of the invention, bean seed and plants produced by the process are first generation ($F_1$) hybrid bean seed and plants produced by crossing a plant in accordance with the invention with another, distinct plant. The present invention further contemplates plant parts of such an $F_1$ hybrid bean plant, and methods of use thereof. Therefore, certain exemplary embodiments of the invention provide an $F_1$ hybrid bean plant and seed thereof.

In still yet another aspect of the invention, the genetic complement of the bean plant line designated RX 08081162 is provided. The phrase "genetic complement" is used to refer to the aggregate of nucleotide sequences, the expression of which sequences defines the phenotype of, in the present case, a bean plant, or a cell or tissue of that plant. A genetic complement thus represents the genetic makeup of a cell, tissue or plant, and a hybrid genetic complement represents the genetic make up of a hybrid cell, tissue or plant. The invention thus provides bean plant cells that have a genetic complement in accordance with the bean plant cells disclosed herein, and plants, seeds and plants containing such cells.

Plant genetic complements may be assessed by genetic marker profiles, and by the expression of phenotypic traits that are characteristic of the expression of the genetic complement, e.g., isozyme typing profiles. It is understood that line RX 08081162 could be identified by any of the many well known techniques such as, for example, Simple Sequence Length Polymorphisms (SSLPs) (Williams et al., *Nucleic Acids Res.*, 1 8:6531-6535, 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., *Science,* 280:1077-1082, 1998).

In still yet another aspect, the present invention provides hybrid genetic complements, as represented by bean plant cells, tissues, plants, and seeds, formed by the combination of a haploid genetic complement of a bean plant of the invention with a haploid genetic complement of a second bean plant, preferably, another, distinct bean plant. In another aspect, the present invention provides a bean plant regenerated from a tissue culture that comprises a hybrid genetic complement of this invention.

In still yet another aspect, the invention provides a plant of an inbred bean line that exhibits a combination of traits including good yield, medium-late maturity, small pod diameter and dark green and glossy pod color. In certain embodiments, the trait may be defined as controlled by genetic means for the expression of the trait found in bean line RX 08081162.

In still yet another aspect, the invention provides a method of determining the genotype of a plant of bean line RX 08081162 comprising detecting in the genome of the plant at least a first polymorphism. The method may, in certain embodiments, comprise detecting a plurality of polymorphisms in the genome of the plant. The method may further comprise storing the results of the step of detecting the plurality of polymorphisms on a computer readable medium. The invention further provides a computer readable medium produced by such a method.

In still yet another aspect, the present invention provides a method of producing a plant derived from line RX 08081162, the method comprising the steps of: (a) preparing a progeny plant derived from line RX 08081162, wherein said preparing comprises crossing a plant of the line RX 08081162 with a second plant; and (b) crossing the progeny plant with itself or a second plant to produce a seed of a progeny plant of a subsequent generation. In further embodiments, the method may additionally comprise: (c) growing a progeny plant of a subsequent generation from said seed of a progeny plant of a subsequent generation and crossing the progeny plant of a subsequent generation with itself or a second plant; and repeating the steps for an additional 3-10 generations to produce a plant derived from line RX 08081162. The plant derived from line RX 08081162 may be an inbred line, and the aforementioned repeated crossing steps may be defined as comprising sufficient inbreeding to produce the inbred line. In the method, it may be desirable to select particular plants resulting from step (c) for continued crossing according to steps (b) and (c). By selecting plants having one or more desirable traits, a plant derived from line RX 08081162 is obtained which possesses some of the desirable traits of the line as well as potentially other selected traits.

In certain embodiments, the present invention provides a method of producing beans comprising: (a) obtaining a plant of bean line RX 08081162, wherein the plant has been cultivated to maturity, and (b) collecting beans from the plant.

These and other features and advantages of this invention are described in, or are apparent from, the following detailed description of various exemplary embodiments of the devices and methods according to this invention.

DETAILED DESCRIPTION OF THE INVENTION

The invention provides methods and compositions relating to plants, seeds and derivatives of the bean line designated RX 08081162. This line shows uniformity and stability within the limits of environmental influence for the traits described hereinafter. Bean line RX 08081162 provides sufficient seed yield. By crossing with a distinct second plant, uniform F1 hybrid progeny can be obtained.

RX 08081162 is a Garden bean (*Phaseolus vulgaris* L.) variety with early maturity and very uniform extra fine sieve pods.

A. ORIGIN AND BREEDING HISTORY OF RX 08081162

The crossing and selections that led directly to RX 08081162 can be summarized as follows:

RX 08081162 was developed by pedigree selection at Monsanto Vegetable seed's Northern European breeding station for open field crops in Wageningen, The Netherlands. It originates from a hand pollinated cross between two breeding lines owned by Seminis, a division of Monsanto.

Female parent (A): 03/12894-1; Inbred breeding line was developed and owned by Monsanto. This line is the variety Bousca (RS08021152). This is an extra fine sieve green bean breeding line with early maturity, high yield and medium extra fine pods of 11.5-13 cm length and medium upright plant habit.

Male parent (B): 03/D478: F5 inbred breeding line developed and owned by Monsanto. This line has a medium maturity, very extra fine sieve pods that are quite short (10.5-11 cm) and have an upright plant habit.

The initial cross was made in the greenhouse in the fall of Year 1. After 8 generations of selfing and pedigree selection, a line was selected that combined the desired extra fine sieve size, pod length of 11-12 cm and upright plant habit.

The breeding and selection scheme was as follows:

| YEAR | SEASON | GENERATION | DESCRIPTION |
|---|---|---|---|
| 1 | Fall | A × B | Cross made |
| 2 | Spring | F1 | Increase, 650 seeds harvested in bulk 04/11206 |
| 2 | Summer | F2 | Planted all seeds from bulk 04/11206 in the field at stake 11552. 62 plants were selected for uniform pod setting and desired pod length. They were harvested as single plant selections. |
| 2 | Winter | F3 | All 62 single plant selections planted at 45 seeds per progeny. 1 line at stake 2588, originating from single plant #41 was selected for its early pod set and good plant habit and harvested in bulk. |
| 3 | Summer | F4 | Planted family 05/2588 in the selection field in Wageningen using 5 × 120 plants per family. Selected 26 single plants from this family at stake number 05D457, and harvested them separately. |
| 3 | Winter | F5 | Planted all 26 single plant selections from 05D457 at 4 seeds per progeny. Harvested single plants. |
| 3 | Winter | F5 | Planted all 26 single plant selections from 05D457 at 45 seeds per progeny. Harvested single plants. Selected five families and harvested them in bulk. |
| 4 | Spring | F6 | Planted the corresponding F6 lines with same origin as selected families in greenhouse at 3 plants per line, resulting in 4 × 3 = 12 single plant selections per selected Chile family. |
| 4 | Summer | F6 | Planted the bulked generation from Chile in the performance trials in The Netherlands and France at 5 × 120 seeds per location. Selected the family at stake 177 as the best one. Selected 21 single plants from this bulk. |
| 4 | Summer | F7 | Planted family all 5 × 12 F6 lines in the selection field in Wageningen using 45 plants per line. Field failed due to weather conditions and was not harvested. |
| 5 | Summer | F7 | Replanted the 21 single plants from 06D277 and the linked greenhouse lines from spring 2006 in the selection field at 45 seeds per line and selected 4 lines for desired performance. Of each selected line 6 single plants and a bulk were harvested. |
| 6 | Summer | F8 | Planted each of the bulks in different performance trials in The Netherlands and France. The family originating from line 07/8426 performed outstandingly. The 6 lines from 07/8426 proved to be uniform and stable in the selection field. No off types were observed. It was coded as RX08081162 and harvested in bulk |
| 6 | Spring | F9 | Planted the 120 plants from the F8 bulk in the greenhouse. Harvested all as single plants. Handed the seed of these 108 lines off to Foundation Seed. |
| 7 | Summer | F10 | Planted all 108 lines from the greenhouse in the Foundation Seed field at 80 seeds per line. The lines proved to be stable and uniform for all described traits. No off types or variants were found. The 108 lines were then bulked. This bulk was used for further increase and multiplication. |

Observations during three generations multiplication and increases in the Netherlands (summer Year 6 and Year 7) and Chile (winter of Year 6), indicate that RX 08081162 is uniform and stable for characteristics including but not limited to plant habit, maturity, pod type and other horticultural and agronomic characteristics. As is true with other garden beans, a very small percentage of mutations for oval pods or string may occur during repeated multiplication. RX 08081162 is within the commercially acceptable limits of 0.1% (for oval pods) and 0.01% (for string) for this type of mutation. No genetic variants have been observed or are expected to occur in future generations of RX 08081162.

B. PHYSIOLOGICAL AND MORPHOLOGICAL CHARACTERISTICS OF BEAN LINE RX 08081162

In accordance with one aspect of the present invention, there is provided a plant having the physiological and morphological characteristics of bean line RX 08081162. A description of the physiological and morphological characteristics of bean line RX 08081162 is presented in Table 1.

TABLE 1

| Physiological and Morphological Characteristics of Line RX 08081162 | | |
|---|---|---|
| Characteristic | RX 08081162 | Angers |
| 1. Type | Garden | Garden |
| 2. Market Maturity | | |
| number of days earlier than comparison variety | 4 | |
| 3. Plant | | |
| number of centimeters spacing between plants in a row | 8 cm | 8 cm |
| habit | determinate | determinate |
| plant height (in centimeters) | 48 cm | 43 cm |
| number of centimeters taller than the comparison variety | 5 cm | |
| plant spread (width) in centimeters | 41 cm | 39 cm |
| number of centimeters wider than the comparison variety | 2 cm | |
| pod position | scattered | scattered |
| bush form | spherical bush form | spherical bush form |
| growth type | dwarf [Callide (D), Capitole (D)] | dwarf [Callide (D), Capitole (D)] |
| dwarf beans only: plant type | non-trailing [Callide (D), Capitole (D)] | non-trailing [Callide (D), Capitole (D)] |
| dwarf beans only: plant height | short [Goldfish (D)] | short [Goldfish (D)] |
| 4. Leaves | | |
| surface | indeterminate | indeterminate |
| size | small (Gitana) | small (Gitana) |
| color | medium green | medium green |
| intensity of green color (at the time of full flowering) | medium [Fori (D), Valja (D)] | medium [Fori (D), Valja (D)] |
| rugosity (at the time of full flowering) | weak [Goldfish (D), Groffy (D), Record (C), Valja (D)] | weak [Goldfish (D), Groffy (D), Record (C), Valja (D)] |
| terminal leaflet: size (at the time of full flowering) | small [Goldfish (D)] | small [Goldfish (D)] |
| terminal leaflet: shape (at the time of full flowering) | circular to rhombic [Calas (D), Capitole (D), Dorabel (D)] | circular to rhombic [Calas (D), Capitole (D), Dorabel (D)] |
| terminal leaflet: length of tip (at the time of full flowering) | long [Flo (D), Nerina (D), Prelude (D)] | long [Flo (D), Nerina (D), Prelude (D)] |
| dwarf beans only: inflorescences: position (at full flowering) | intermediate [Tuf (D), Valja (D)] | intermediate [Tuf (D), Valja (D)] |
| plant: anthocyanin coloration of hypocotyl | absent [Tuf (D)] | absent [Tuf (D)] |
| 5. Anthocyanin Pigment: | | |
| flowers | absent | absent |
| leaves | absent | absent |
| stems | absent | absent |
| petioles | absent | absent |
| pods | absent | absent |
| peduncles | absent | absent |
| seeds | absent | absent |
| nodes | absent | absent |

TABLE 1-continued

Physiological and Morphological Characteristics of Line RX 08081162

| Characteristic | RX 08081162 | Angers |
| --- | --- | --- |
| 6. Flower | | |
| size of bracts | small [Fanion (C), Fidel (C), Markant (C), Nernia (D), Ryco (D)] | small [Fanion (C), Fidel (C), Markant (C), Nernia (D), Ryco (D)] |
| color of standard | white [Tuf (D)] | white [Tuf (D)] |
| color of wings | white [Tuf (D)] | white [Tuf (D)] |
| color of keel | white | white |
| number of days to 50% bloom | 54 | 56 |
| 7. Pods | | |
| exterior color (fresh) (at edible maturity) | medium green | medium green |
| processed pods (exterior color) (at edible maturity) | dark (Bush Blue Lake 290) | dark (Bush Blue Lake 290) |
| dry pod color (at edible maturity) | buckskin (Sprite) | buckskin (Sprite) |
| dwarf beans only: Pod length (excluding beak) (at the time of fresh market maturity) | medium [Amity (D), Luisa (D)[ | medium [Amity (D), Luisa (D)[ |
| width (at the time of fresh market maturity) | narrow [Cabri (D), Necores (C), Tuf (D)] | narrow [Cabri (D), Necores (C), Tuf (D)] |
| thickness (at the time of fresh market maturity) | very thin [Booster (D)] | very thin [Booster (D)] |
| ratio thickness/width (at the time of fresh market maturity) | medium [Tuf (D)] | medium [Tuf (D)] |
| shape in cross section (through seed in middle of pod) (at the time of fresh market maturity) | circular or round | circular or round |
| crease back | absent | absent |
| pubescence | none (Slenderette) | none (Slenderette) |
| constriction (interlocular cavitation) at dry seed stage | moderate | moderate |
| spur length | 10 mm | 12 mm |
| fiber | sparse | sparse |
| number of seeds per pod | 7 | 7 |
| stringiness of ventral suture (at the time of fresh market maturity) | absent [Cabri (D), Tuf (D)] | absent [Cabri (D), Tuf (D)] |
| seed development | slow (Bush Blue Lake 290) | slow (Bush Blue Lake 290) |
| machine harvest | adapted | adapted |
| percent sieve size distribution at optimum maturity for non-flat pods | | |
| 4.76 to 5.76 | 20% | |
| 5.76 to 7.34 | 80% | |
| 7.34 to 8.34 | 0% | |
| 8.34 to 9.53 mm | 0% | |
| 9.53 to 10.72 MM | 0% | |
| >10.72 mm | 0% | |
| 3 Sieve | 11.8 cm length; 6.7 mm width; 6.7 total mm thickness | |
| ground color (at the time of fresh market maturity) | green [Diva (D), Filetty (D), Fortissima (C)] | green [Diva (D), Filetty (D), Fortissima (C)] |
| intensity of ground color (at the time of fresh market maturity) | medium [Gabriella (D), Filetty (D), Prelude (D)] | medium [Gabriella (D), Filetty (D), Prelude (D)] |
| presence of secondary color (at the dry seed stage) | absent [Tuf (D)] | absent [Tuf (D)] |
| degree of curvature (at the time of fresh market maturity) | weak [Nerina (D)] | weak [Nerina (D)] |
| shape of curvature (at the time of fresh market maturity) | convex (Calima (D)] | convex (Calima (D)] |
| shape of distal part (excluding beak) (at the time of fresh market maturity) | acute [Aiguillon (D), Calas (D), Cesar (D)] | acute [Aiguillon (D), Calas (D), Cesar (D)] |

TABLE 1-continued

Physiological and Morphological Characteristics of Line RX 08081162

| Characteristic | RX 08081162 | Angers |
|---|---|---|
| length of beak (at the time of fresh market maturity) | medium [Goldfish (D), Optimus (D)] | medium [Goldfish (D), Optimus (D)] |
| curvature of beak (at the time of fresh market maturity) | weak [Nerina (D)] | weak [Nerina (D)] |
| texture of surface (at the time of fresh market maturity) | smooth or slightly rough [Prelude (D), Tuf (D)] | smooth or slightly rough [Prelude (D), Tuf (D)] |
| 8. Seed | | |
| seed: weight | very low [Cabri (D), Decibel (D), Label (D)] | very low [Cabri (D), Decibel (D), Label (D)] |
| seed color: seed coat luster | semi-shiny | semi-shiny |
| seed color: seed coat | monochrome | monochrome |
| seed: number of colors (of dry harvested seed) | one | one |
| main/primary color (largest area) (of dry harvested seed) | white | white |
| seed coat pattern | solid | solid |
| seed: veining (of dry harvested seed) | weak [Prelude (D), Ryco (D)] | weak [Prelude (D), Ryco (D)] |
| seed color: hilar ring | absent | absent |
| 9. Seed Shape and Size | | |
| hilum view | elliptical | oval |
| side view | oval to oblong | oval to oblong |
| seed: shape in longitudinal section (of dry harvested seed) | elliptic [Nerina (D), Pros (D), Tuf (D)] | elliptic [Nerina (D), Pros (D), Tuf (D)] |
| seed: shape in cross section (of dry harvested seed) | circular [Pactol (D), Romulus (D), Stamel (D)] | circular [Pactol (D), Romulus (D), Stamel (D)] |
| seed: width in cross section (of dry harvested seed) | narrow [Cabri (D), Golddukat (D)] | narrow [Cabri (D), Golddukat (D)] |
| seed: length (of dry harvested seed) | medium [Igolomska (D)] | short [Raba (D)] |
| gm/100 seeds, grams per 100 seeds | 11.4 gm | 10.0 gm |
| gm/100 seeds, grams per 100 seeds heavier than the comparison variety | 1.4 gm | |
| time of flowering (50% of the plants with at least one flower) | medium [Fanion (D), Groffy (D), Hilda (C), Precores (C)] | medium [Fanion (D), Groffy (D), Hilda (C), Precores (C)] |

*These are typical values. Values may vary due to environment. Other values that are substantially equivalent are within the scope of the invention.

C. BREEDING BEAN LINE RX 08081162

One aspect of the current invention concerns methods for crossing the bean line RX 08081162 with itself or a second plant and the seeds and plants produced by such methods. These methods can be used for propagation of line RX 08081162, or can be used to produce hybrid bean seeds and the plants grown therefrom. Hybrid seeds are produced by crossing line RX 08081162 with second bean parent line.

The development of new varieties using one or more starting varieties is well known in the art. In accordance with the invention, novel varieties may be created by crossing line RX 08081162 followed by multiple generations of breeding according to such well known methods. New varieties may be created by crossing with any second plant. In selecting such a second plant to cross for the purpose of developing novel lines, it may be desired to choose those plants which either themselves exhibit one or more selected desirable characteristics or which exhibit the desired characteristic(s) in progeny. Once initial crosses have been made, inbreeding and selection take place to produce new varieties. For development of a uniform line, often five or more generations of selfing and selection are involved.

Uniform lines of new varieties may also be developed by way of double-haploids. This technique allows the creation of true breeding lines without the need for multiple generations of selfing and selection. In this manner, true breeding lines can be produced in as little as one generation. Haploid embryos may be produced from microspores, pollen, anther cultures, or ovary cultures. The haploid embryos may then be doubled autonomously, or by chemical treatments (e.g. colchicine treatment). Alternatively, haploid embryos may be grown into haploid plants and treated to induce chromosome doubling. In either case, fertile homozygous plants are obtained. In accordance with the invention, any of such techniques may be used in connection with line RX 08081162 and progeny thereof to achieve a homozygous line.

New varieties may be created, for example, by crossing line RX 08081162 with any second plant and selection of progeny in various generations and/or by doubled haploid technology. In choosing a second plant to cross for the purpose of developing novel lines, it may be desired to choose those plants which either themselves exhibit one or more selected desirable characteristics or which exhibit the desired characteristic(s) in progeny. After one or more lines are crossed, true-breeding lines may be developed.

Backcrossing can also be used to improve an inbred plant. Backcrossing transfers a specific desirable trait from one inbred or non-inbred source to an inbred that lacks that trait. This can be accomplished, for example, by first crossing a superior inbred (A) (recurrent parent) to a donor inbred (non-recurrent parent), which carries the appropriate locus or loci for the trait in question. The progeny of this cross are then mated back to the superior recurrent parent (A) followed by selection in the resultant progeny for the desired trait to be transferred from the non-recurrent parent. After five or more backcross generations with selection for the desired trait, the progeny are heterozygous for loci controlling the characteristic being transferred, but are like the superior parent for most or almost all other loci. The last backcross generation would be selfed to give pure breeding progeny for the trait being transferred.

The line of the present invention is particularly well suited for the development of new lines based on the elite nature of the genetic background of the line. In selecting a second plant to cross with RX 08081162 for the purpose of developing novel bean lines, it will typically be preferred to choose those plants which either themselves exhibit one or more selected desirable characteristics or which exhibit the desired characteristic(s) when in hybrid combination. Examples of desirable characteristics may include, for example, seed yield, seed size, seed shape, seed uniformity, pod size, pod shape, pod color, pod uniformity, early maturity, disease resistance, herbicide tolerance, seedling vigor, adaptability for soil conditions, adaptability for climate conditions, and uniform plant height.

D. PERFORMANCE CHARACTERISTICS

Performance characteristics of the line RX 08081162 were the subject of an objective analysis of the performance traits of the line relative to other lines. Results from the analysis are presented in Table 2.

TABLE 2

Performance characteristics comparison between RX 08081162 and Comparative varieties.

| Row Labels | G days | Yield t/ha | % XF | % TF | Uniformity | General Impression |
|---|---|---|---|---|---|---|
| First sowing | 66.8 | 15.6 | 71.0 | 29.0 | 2.9 | 3.3 |
| Bousca | 66.2 | 16.5 | 43.1 | 56.9 | 2.7 | 3.3 |
| Carthage | 69.0 | 17.1 | 100.0 | 0.0 | 3.3 | 3.7 |
| RX08081162 | 66.2 | 13.8 | 81.6 | 18.4 | 2.8 | 3.2 |
| Second sowing | 70.6 | 19.5 | 58.2 | 41.8 | 3.0 | 3.4 |
| Bousca | 69.8 | 21.5 | 29.5 | 70.5 | 3.3 | 3.9 |
| Carthage | 72.5 | 17.9 | 80.5 | 19.5 | 2.9 | 3.3 |
| RX08081162 | 69.8 | 18.7 | 69.1 | 30.9 | 2.8 | 3.0 |
| Third sowing | 73.6 | 21.2 | 45.4 | 54.6 | 3.4 | 3.7 |
| Bousca | 72.6 | 23.6 | 20.0 | 80.0 | 3.6 | 3.9 |
| Carthage | 75.5 | 19.1 | 62.1 | 37.9 | 3.4 | 3.5 |
| RX08081162 | 73.0 | 20.5 | 58.8 | 41.2 | 3.1 | 3.7 |
| Grand Total | 70.4 | 18.8 | 58.1 | 41.9 | 3.1 | 3.5 |

% XF = % pods between 5 and 6.5 mm. diameter in total pod weight.
G days = Growing days from sowing to harvest.
% TF = % pods between 6 and 8 mm. diameter in total pod weight.
GENERAL IMPRESSION = overall rating for pod quality and appearance.

E. FURTHER EMBODIMENTS OF THE INVENTION

In certain aspects of the invention, plants described herein are provided modified to include at least a first desired heritable trait. Such plants may, in one embodiment, be developed by a plant breeding technique called backcrossing, wherein essentially all of the morphological and physiological characteristics of a variety are recovered in addition to a genetic locus transferred into the plant via the backcrossing technique. The term single locus converted plant as used herein refers to those bean plants which are developed by a plant breeding technique called backcrossing, wherein essentially all of the desired morphological and physiological characteristics of a variety are recovered in addition to the single locus transferred into the variety via the backcrossing technique.

Backcrossing methods can be used with the present invention to improve or introduce a characteristic into the present variety. The parental bean plant which contributes the locus for the desired characteristic is termed the nonrecurrent or donor parent. This terminology refers to the fact that the nonrecurrent parent is used one time in the backcross protocol and therefore does not recur. The parental bean plant to which the locus or loci from the nonrecurrent parent are transferred is known as the recurrent parent as it is used for several rounds in the backcrossing protocol.

In a typical backcross protocol, the original variety of interest (recurrent parent) is crossed to a second variety (nonrecurrent parent) that carries the single locus of interest to be transferred. The resulting progeny from this cross are then crossed again to the recurrent parent and the process is repeated until a bean plant is obtained wherein essentially all of the desired morphological and physiological characteristics of the recurrent parent are recovered in the converted plant, in addition to the single transferred locus from the nonrecurrent parent.

The selection of a suitable recurrent parent is an important step for a successful backcrossing procedure. The goal of a backcross protocol is to alter or substitute a single trait or characteristic in the original variety. To accomplish this, a single locus of the recurrent variety is modified or substituted with the desired locus from the nonrecurrent parent, while retaining essentially all of the rest of the desired genetic, and therefore the desired physiological and morphological constitution of the original variety. The choice of the particular nonrecurrent parent will depend on the purpose of the backcross; one of the major purposes is to add some commercially desirable trait to the plant. The exact backcrossing protocol will depend on the characteristic or trait being altered and the genetic distance between the recurrent and nonrecurrent parents. Although backcrossing methods are simplified when the characteristic being transferred is a dominant allele, a recessive allele may also be transferred. In this instance it may be necessary to introduce a test of the progeny to determine if the desired characteristic has been successfully transferred.

In one embodiment, progeny bean plants of a backcross in which RX 08081162 is the recurrent parent comprise (i) the desired trait from the non-recurrent parent and (ii) all of the physiological and morphological characteristics of bean line RX 08081162 as determined at the 5% significance level when grown in the same environmental conditions.

Bean varieties can also be developed from more than two parents. The technique, known as modified backcrossing, uses different recurrent parents during the backcrossing. Modified backcrossing may be used to replace the original recurrent parent with a variety having certain more desirable characteristics or multiple parents may be used to obtain different desirable characteristics from each.

With the development of molecular markers associated with particular traits, it is possible to add additional traits into an established germ line, such as represented here, with the end result being substantially the same base germplasm with the addition of a new trait or traits. Molecular breeding, as described in Moose and Mumm, 2008 (Plant Physiology, 147: 969-977), for example, and elsewhere, provides a mechanism for integrating single or multiple traits or QTL into an elite line. This molecular breeding-facilitated movement of a trait or traits into an elite line may encompass incorporation of a particular genomic fragment associated with a particular trait of interest into the elite line by the mechanism of identification of the integrated genomic fragment with the use of flanking or associated marker assays. In the embodiment represented here, one, two, three or four genomic loci, for example, may be integrated into an elite line via this methodology. When this elite line containing the additional loci is further crossed with another parental elite line to produce hybrid offspring, it is possible to then incorporate at least eight separate additional loci into the hybrid. These additional loci may confer, for example, such traits as a disease resistance or a fruit quality trait. In one embodiment, each locus may confer a separate trait. In another embodiment, loci may need to be homozygous and exist in each parent line to confer a trait in the hybrid. In yet another embodiment, multiple loci may be combined to confer a single robust phenotype of a desired trait.

Many single locus traits have been identified that are not regularly selected for in the development of a new inbred but that can be improved by backcrossing techniques. Single locus traits may or may not be transgenic; examples of these traits include, but are not limited to, male sterility, herbicide resistance, resistance to bacterial, fungal, or viral disease, insect resistance, restoration of male fertility, modified fatty acid or carbohydrate metabolism, and enhanced nutritional quality. These comprise genes generally inherited through the nucleus.

Direct selection may be applied where the single locus acts as a dominant trait. An example of a dominant trait is the anthracnose resistance trait. For this selection process, the progeny of the initial cross are sprayed with anthracnose spores prior to the backcrossing. The spraying eliminates any plants which do not have the desired anthracnose resistance characteristic, and only those plants which have the anthracnose resistance gene are used in the subsequent backcross. This process is then repeated for all additional backcross generations.

Selection of bean plants for breeding is not necessarily dependent on the phenotype of a plant and instead can be based on genetic investigations. For example, one can utilize a suitable genetic marker which is closely genetically linked to a trait of interest. One of these markers can be used to identify the presence or absence of a trait in the offspring of a particular cross, and can be used in selection of progeny for continued breeding. This technique is commonly referred to as marker assisted selection. Any other type of genetic marker or other assay which is able to identify the relative presence or absence of a trait of interest in a plant can also be useful for breeding purposes. Procedures for marker assisted selection applicable to the breeding of bean are well known in the art. Such methods will be of particular utility in the case of recessive traits and variable phenotypes, or where conventional assays may be more expensive, time consuming or otherwise disadvantageous. Types of genetic markers which could be used in accordance with the invention include, but are not necessarily limited to, Simple Sequence Length Polymorphisms (SSLPs) (Williams et al., *Nucleic Acids Res.*, 18:6531-6535, 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., *Science*, 280:1077-1082, 1998).

F. PLANTS DERIVED FROM BEAN LINE RX 08081162 BY GENETIC ENGINEERING

Many useful traits that can be introduced by backcrossing, as well as directly into a plant, are those which are introduced by genetic transformation techniques. Genetic transformation may therefore be used to insert a selected transgene into the bean line of the invention or may, alternatively, be used for the preparation of transgenes which can be introduced by backcrossing. Methods for the transformation of plants, including bean, are well known to those of skill in the art. Techniques which may be employed for the genetic transformation of bean include, but are not limited to, electroporation, microprojectile bombardment, *Agrobacterium*-mediated transformation and direct DNA uptake by protoplasts.

As is well known in the art, tissue culture of bean can be used for the in vitro regeneration of a bean plant. Tissue culture of various tissues of beans and regeneration of plants there from is well known. For example, reference may be had to McClean and Grafton (*Plant Sci.*, 60:117-122, 1989); Mergeai and Baudoin (*B.I.C. Invit. Papers*, 33:115-116, 1990); Vanderwesthuizen and Groenewald (*S. Afr. J. Bot.*, 56:271-273, 1990); Benedicic et al. (*Plant Cell Tissue Org. Cult.*, 24:199-206, 1990); Malik and Saxena (*Planta*, 184(1):148-150, 1991).

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

A particularly efficient method for delivering transforming DNA segments to plant cells is microprojectile bombardment. In this method, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a surface covered with target bean cells. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large.

Microprojectile bombardment techniques are widely applicable, and may be used to transform virtually any plant species. For example, Russell et al. (*Plant Cell Reports*, 12(3):165-169, 1993).

*Agrobacterium*-mediated transfer is another widely applicable system for introducing gene loci into plant cells. An advantage of the technique is that DNA can be introduced into whole plant tissues, thereby bypassing the need for regeneration of an intact plant from a protoplast. Modern *Agrobacterium* transformation vectors are capable of replication in *E. coli* as well as *Agrobacterium*, allowing for convenient manipulations (Klee et al., *Bio-Technology*, 3(7):637-642, 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described have convenient multi-linker regions flanked by a promoter and a polyadenylation site for direct expression of inserted polypeptide coding genes. Additionally, *Agrobacterium* containing both armed and disarmed Ti genes can be used for transformation.

In those plant strains where *Agrobacterium*-mediated transformation is efficient, it is the method of choice because of the facile and defined nature of the gene locus transfer. The use of *Agrobacterium*-mediated plant integrating vectors to introduce DNA into plant cells is well known in the art (Fraley et al., *Bio/Technology*, 3:629-635, 1985; U.S. Pat. No. 5,563,055). *Agrobacterium*-mediated transformation of *P. vulgaris* is described in, for example, Zhang et al. (*J. American Soc. Horticul. Sci.*, 122(3):300-305, 1997); McClean et al. (*Plant Cell Tiss. Org. Cult.*, 24:131-138, 1991); Lewis and Bliss (*J. American Soc. Horticul. Sci.*, 119:361-366, 1994); and Song et al. (*J. Plant Physiol.*, 146:148-154, 1995).

Transformation of plant protoplasts also can be achieved using methods based on calcium phosphate precipitation, polyethylene glycol treatment, electroporation, and combinations of these treatments (see, e.g., Potrykus et al., *Mol. Gen. Genet.*, 199:183-188, 1985; Omirulleh et al., *Plant Mol. Biol.*, 21(3):415-428, 1993; Fromm et al., *Nature*, 312:791-793, 1986; Uchimiya et al., *Mol. Gen. Genet.*, 204:204, 1986; Marcotte et al., *Nature*, 335:454, 1988). Transformation of plants and expression of foreign genetic elements is exemplified in Choi et al. (*Plant Cell Rep.*, 13: 344-348, 1994), and Ellul et al. (*Theor. Appl. Genet.*, 107:462-469, 2003).

A number of promoters have utility for plant gene expression for any gene of interest including but not limited to selectable markers, scoreable markers, genes for pest tolerance, disease resistance, nutritional enhancements and any other gene of agronomic interest. Examples of constitutive promoters useful for garden bean plant gene expression include, but are not limited to, the cauliflower mosaic virus (CaMV) P-35S promoter, which confers constitutive, high-level expression in most plant tissues (see, e.g., Odel et al., *Nature*, 313:810, 1985), including monocots (see, e.g., Dekeyser et al., *Plant Cell*, 2:591, 1990; Terada and Shimamoto, *Mol. Gen. Genet.*, 220:389, 1990); a tandemly duplicated version of the CaMV 35S promoter, the enhanced 35S promoter (P-e35S) the nopaline synthase promoter (An et al., *Plant Physiol.*, 88:547, 1988), the octopine synthase promoter (Fromm et al., *Plant Cell*, 1:977, 1989); and the figwort mosaic virus (P-FMV) promoter as described in U.S. Pat. No. 5,378,619 and an enhanced version of the FMV promoter (P-eFMV) where the promoter sequence of P-FMV is duplicated in tandem, the cauliflower mosaic virus 19S promoter, a sugarcane bacilliform virus promoter, a commelina yellow mottle virus promoter, and other plant DNA virus promoters known to express in plant cells.

With an inducible promoter the rate of transcription increases in response to an inducing agent. Any inducible promoter can be used in the instant invention. A variety of plant gene promoters that are regulated in response to environmental, hormonal, chemical, and/or developmental signals can be used for expression of an operably linked gene in plant cells, including promoters regulated by (1) heat (Callis et al., *Plant Physiol.*, 88:965, 1988), (2) light (e.g., pea rbcS-3A promoter, Kuhlemeier et al., *Plant Cell*, 1:471, 1989; maize rbcS promoter, Schaffner and Sheen, *Plant Cell*, 3:997, 1991; or chlorophyll a/b-binding protein promoter, Simpson et al., *EMBO J.*, 4:2723, 1985), (3) hormones, such as abscisic acid (Marcotte et al., *Plant Cell*, 1:969, 1989), (4) wounding (e.g., wunl, Siebertz et al., *Plant Cell*, 1:961, 1989); or (5) chemicals such as methyl jasmonate, salicylic acid, or Safener. It may also be advantageous to employ organ-specific promoters (e.g., Roshal et al., *EMBO J.*, 6:1155, 1987; Schernthaner et al., *EMBO J.*, 7:1249, 1988; Bustos et al., *Plant Cell*, 1:839, 1989). Exemplary organ-specific or organ-preferred promoters include, but are not limited to, a root-preferred promoter, such as that from the phaseolin gene (Sengupta-Gopalan et al., *Proc. Natl. Acad. Sci. USA*, 82:3320-3324, 1985); a leaf-specific and light-induced promoter such as that from cab or rubisco (Simpson et al., *EMBO J.*, 4:2723, 1985) and Timko et al., *Nature*, 318:579-582, 1985); an anther-specific promoter such as that from LAT52 (Twell et al., *Mol. Gen. Genetics*, 217:240-245, 1989); a pollen-specific promoter such as that from Zm13 (Guerrero et al., *Mol. Gen. Genetics*, 244:161-168, 1993) or a microspore-preferred promoter such as that from apg (Twell et al., *Sex. Plant Reprod.*, 6:217-224, 1993).

Transport of protein produced by transgenes to a subcellular compartment such as the chloroplast, vacuole, peroxisome, glyoxysome, cell wall, or mitochondrion or for secretion into the apoplast, may be accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized. The presence of a signal sequence directs a polypeptide to either an intracellular organelle or subcellular compartment or for secretion to the apoplast. Many signal sequences are known in the art. See, for example Becker et al. (*Plant Mol. Biol.*, 20:49, 1992); Knox et al. (*Plant Mol. Biol.*, 9:3-17, 1987); Lerner et al. (*Plant Physiol.*, 91:124-129, 1989); Fontes et al. (*Plant Cell*, 3:483-496, 1991); Matsuoka et al. (*Proc. Natl. Acad. Sci. USA*, 88:834, 1991); Gould et al. (*J. Cell. Biol.*, 108:1657, 1989); Creissen et al. (*Plant J.*, 2:129, 1991); Kalderon et al. (*Cell*, 39:499-509, 1984); Steifel et al. (*Plant Cell*, 2:785-793, 1990).

Exemplary nucleic acids which may be introduced to the bean lines of this invention include, for example, DNA sequences or genes from another species, or even genes or sequences which originate with or are present in the same species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into a bean plant according to the invention. Non-limiting examples of particular genes and corresponding phenotypes one may choose to introduce into a bean plant include one or more genes for insect tolerance, such as a *Bacillus thuringiensis* (B.t.) gene, pest tolerance such as genes for fungal disease control, herbicide tolerance such as genes conferring glyphosate tolerance, and genes for quality improvements such as yield, nutritional enhancements, environmental or stress tolerances, or any desirable changes in plant physiology, growth, development, morphology or plant product(s). For example, structural genes would include any gene that confers insect tolerance including but not limited to a *Bacillus* insect control protein gene as described in WO 99/31248, herein incorporated by reference in its entirety, U.S. Pat. No. 5,689,052, herein incorporated by reference in its entirety, U.S. Pat. Nos. 5,500,365 and 5,880,275, herein incorporated by reference it their entirety. In another embodiment, the structural gene can confer tolerance to the herbicide glyphosate as conferred by genes including, but not limited to *Agrobacterium* strain CP4 glyphosate resistant EPSPS gene (aroA:CP4) as described in U.S. Pat. No. 5,633,435, herein incorporated by reference in its entirety, or glyphosate oxidoreductase gene (GOX) as described in U.S. Pat. No. 5,463,175, herein incorporated by reference in its entirety.

Alternatively, the DNA coding sequences can affect these phenotypes by encoding a non-translatable RNA molecule that causes the targeted inhibition of expression of an endogenous gene, for example via antisense- or cosuppression-mediated mechanisms (see, for example, Bird et al., *Biotech. Gen. Engin. Rev.*, 9:207, 1991). The RNA could also be a catalytic RNA molecule (i.e., a ribozyme) engineered to cleave a desired endogenous mRNA product (see for example, Gibson and Shillito, *Mol. Biotech.*, 7:125, 1997). Thus, any gene which produces a protein or mRNA which expresses a phenotype or morphology change of interest is useful for the practice of the present invention.

G. DEFINITIONS

In the description and tables herein, a number of terms are used. In order to provide a clear and consistent understanding of the specification and claims, the following definitions are provided:

A: When used in conjunction with the word "comprising" or other open language in the claims, the words "a" and "an" denote "one or more."

Allele: Any of one or more alternative forms of a gene locus, all of which alleles relate to one trait or characteristic. In a diploid cell or organism, the two alleles of a given gene occupy corresponding loci on a pair of homologous chromosomes.

Backcrossing: A process in which a breeder repeatedly crosses hybrid progeny, for example a first generation hybrid ($F_1$), back to one of the parents of the hybrid progeny. Backcrossing can be used to introduce one or more single locus conversions from one genetic background into another.

Bean Yield (Tons/Acre): The recovered yield in tons/acre is the yield of the bean pods at harvest versus the means of harvest (hand picked, mechanical harvest).

Broad Adaptation: A cultivar having a broad adaptability means a cultivar or selection that will perform well in different growing conditions, locations, and seasons.

Bush Form: A USDA term about the visual look of the plant. A bean plant is: Spherical (even in width and height), Wide when the bush is wider than tall, High when the bush is taller than wide, or Stem when the individual branches protrude from the shape.

Concentrated set of pods: A concentrated set of pods is said of a plant where a high percentage of all pods on a plant set and mature at the same time so as to facilitate a single harvest.

Crossing: The mating of two parent plants.

Cross-pollination: Fertilization by the union of two gametes from different plants.

Determinate plant: A determinate plant will grow to a fixed number of nodes with a terminal floral raceme on the main stem, while an indeterminate plant continues to grow and never has a terminal floral raceme on the main stem.

Diploid: A cell or organism having two sets of chromosomes.

Dry pod color: The color of dry pods can be Buckskin (a light to pale brown), Salmon (a distinct reddish color), or Green (pale to intense) depending on the expression of the gene for persistent green.

Emasculate: The removal of plant male sex organs or the inactivation of the organs with a cytoplasmic or nuclear genetic factor or a chemical agent conferring male sterility.

Enzymes: Molecules which can act as catalysts in biological reactions.

$F_1$ Hybrid: The first generation progeny of the cross of two nonisogenic plants.

Field holding ability: A bean plant that has field holding ability means a plant having pods that remain smooth and retain their color along with a firm fleshy interior as the seed approached physiological maturity.

Genotype: The genetic constitution of a cell or organism.

Haploid: A cell or organism having one set of the two sets of chromosomes in a diploid.

Linkage: A phenomenon wherein alleles on the same chromosome tend to segregate together more often than expected by chance if their transmission was independent.

Machine or mechanical harvest: A machine harvestable plant means a bean plant from which the pods can be removed from the plant one of several commercial mechanical harvesters in such a manner as to reduce broken pods, clusters, and plant matter from the desired pods.

Marker: A readily detectable phenotype, preferably inherited in codominant fashion (both alleles at a locus in a diploid heterozygote are readily detectable), with no environmental variance component, i.e., heritability of 1.

Maturity: A maturity under 53 days is considered early while one between 54-59 days would be considered average or medium and one of 60 or more days would be late.

Maturity Date: Plants are considered mature when the pods have reached their maximum desirable seed size and sieve size for the specific use intended. This can vary for each end user, e.g., processing at different stages of maturity would be required for different types of consumer beans such as "whole pack," "cut" or "French style." The number of days is calculated from a relative planting date which depends on day length, heat units and other environmental factors.

Phenotype: The detectable characteristics of a cell or organism, which characteristics are the manifestation of gene expression.

Pod Color: A USDA term where light green color is defined by the variety Provider and a dark green color by the variety Bush Blue Lake 290. Yellow is defined as color of the wax bean Goldrush.

Pod Position: The pod position is the location of the pods within the plant. The pods can be high (near the top), low (near the bottom), or medium (in the middle) of the plant, or scattered throughout the plant.

Quantitative Trait Loci (QTL): Quantitative trait loci (QTL) refer to genetic loci that control to some degree numerically representable traits that are usually continuously distributed.

Regeneration: The development of a plant from tissue culture.

Resistance: As used herein, the terms "resistance" and "tolerance" are used interchangeably to describe plants that show no symptoms to a specified biotic pest, pathogen, abiotic influence or environmental condition. These terms are also used to describe plants showing some symptoms but that are still able to produce marketable product with an acceptable yield. Some plants that are referred to as resistant or tolerant are only so in the sense that they may still produce a crop, even though the plants are stunted and the yield is reduced.

Royal Horticultural Society (RHS) color chart value: The RHS color chart is a standardized reference which allows accurate identification of any color. A color's designation on the chart describes its hue, brightness and saturation. A color is precisely named by the RHS color chart by identifying the group name, sheet number and letter, e.g., Yellow-Orange Group 19A or Red Group 41B.

Seed development: The rate at which seeds develop as pods reach their harvest diameter. A slow seed development characteristic will give a cultivar its field holding ability, and a larger harvest window.

Self-pollination: The transfer of pollen from the anther to the stigma of the same plant.

Single Locus Converted (Conversion) Plant: Plants which are developed by a plant breeding technique called backcrossing wherein essentially all of the morphological and physiological characteristics of an inbred are recovered in addition to the characteristics conferred by the single locus transferred into the inbred via the backcrossing technique. By "essentially all," it is meant that all of the characteristics of a plant are recovered that are otherwise present when compared in the same environment and save for the converted locus, other than an occasional variant trait that might arise during backcrossing or direct introduction of a transgene. A single locus may comprise one gene, or in the case of transgenic plants, one or more transgenes integrated into the host genome at a single site (locus).

Substantially Equivalent: A characteristic that, when compared, does not show a statistically significant difference (e.g., p=0.05) from the mean.

Tetraploid: A cell or organism having four sets of chromosomes.

Tissue Culture: A composition comprising isolated cells of the same or a different type or a collection of such cells organized into parts of a plant.

Transgene: A genetic locus comprising a sequence which has been introduced into the genome of a garden bean plant by transformation.

Triploid: A cell or organism having three sets of chromosomes.

H. DEPOSIT INFORMATION

A deposit of bean line RX 08081162, disclosed above and recited in the claims, has been made with the American Type Culture Collection (ATCC), 10801 University Blvd., Manassas, Va. 20110-2209, USA, and assigned ATCC Accession No. PTA-12609. The seeds were deposited with the ATCC on Mar. 1, 2012. Access to this deposit will be available during the pendency of the application to the Commissioner of Patents and Trademarks and persons determined by the Commissioner to be entitled thereto upon request. The deposits will be maintained in the ATCC Depository, which is a public depository, for a period of 30 years, or 5 years after the most recent request, or for the enforceable life of the patent, whichever is longer, and will be replaced if it becomes nonviable during that period. Applicant does not waive rights granted under this patent or under the Plant Variety Protection Act (7 U.S.C. 2321 et seq.).

Although the foregoing invention has been described in detail by way of illustration and example for purposes of clarity and understanding, it will be obvious that certain changes and modifications may be practiced within the scope of the invention, as limited only by the scope of the appended claims.

All references cited herein are hereby expressly incorporated herein by reference.

What is claimed is:

1. A seed of bean line RX 08081162, a sample of seed of said line having been deposited under ATCC Accession Number PTA-12609.

2. A plant of bean line RX 08081162, a sample of seed of said line having been deposited under ATCC Accession Number PTA-12609.

3. A plant part of the plant of claim 2.

4. The plant part of claim 3, wherein said part is selected from the group consisting of a pod, pollen, an ovule and a cell.

5. A bean plant, or a part thereof, having all the physiological and morphological characteristics of the bean plant of claim 2.

6. A tissue culture of regenerable cells of bean line RX 08081162, a sample of seed of said line having been deposited under ATCC Accession Number PTA-12609.

7. The tissue culture according to claim 6, comprising cells or protoplasts from a plant part selected from the group consisting of embryos, meristems, cotyledons, pollen, leaves, anthers, roots, root tips, pistil, flower, seed and stalks.

8. A bean plant regenerated from the tissue culture of claim 6, wherein the regenerated plant expresses all of the physiological and morphological characteristics of bean line RX 08081162, a sample of seed of said line having been deposited under ATCC Accession Number PTA-12609.

9. A method of producing bean seed, comprising crossing the plant of claim 2 with itself or a second bean plant.

10. The method of claim 9, wherein the plant of bean line RX 08081162 is the female parent.

11. The method of claim 9, wherein the plant of bean line RX 08081162 is the male parent.

12. An F1 hybrid seed produced by the method of claim 9.

13. An F1 hybrid plant produced by growing the seed of claim 12.

14. A method for producing a seed of a line RX 08081162-derived bean plant comprising the steps of:
   (a) crossing a bean plant of line RX 08081162 with a second bean plant, a sample of seed of said line having been deposited under ATCC Accession Number PTA-12609; and
   (b) allowing seed of a RX 08081162-derived bean plant to form.

15. The method of claim 14, further comprising the steps of:
   (c) crossing a plant grown from said RX 08081162-derived bean seed with itself or a second bean plant to yield additional RX 08081162-derived bean seed;

(d) growing said additional RX 08081162-derived bean seed of step (c) to yield additional RX 08081162-derived bean plants; and (e) repeating the crossing and growing steps of (c) and (d) to generate further RX 08081162-derived bean plants.

16. A method of vegetatively propagating a plant of bean line RX 08081162 comprising the steps of:

(a) collecting tissue capable of being propagated from a plant of bean line RX 08081162, a sample of seed of said line having been deposited under ATCC Accession Number PTA-12609;

(b) cultivating said tissue to obtain proliferated shoots; and (c) rooting said proliferated shoots to obtain rooted plantlets.

17. The method of claim 16, further comprising growing plants from said rooted plantlets.

18. A method of introducing a desired trait into bean line RX 08081162 comprising:

(a) crossing a plant of line RX 08081162 with a second bean plant that comprises a desired trait to produce F1 progeny, a sample of seed of said line RX 08081162 having been deposited under ATCC Accession Number PTA-12609;

(b) selecting an F1 progeny that comprises the desired trait;

(c) crossing the selected F1 progeny with a plant of line RX 08081162 to produce backcross progeny;

(d) selecting backcross progeny comprising the desired trait and the physiological and morphological characteristic of bean line RX 08081162; and (e) repeating steps (c) and (d) three or more times to produce selected fourth or higher backcross progeny that comprise the desired trait and essentially all of the physiological and morphological characteristics of bean line RX 08081162 when grown in the same environmental conditions.

19. A bean plant produced by the method of claim 18.

20. A method of producing a plant of bean line RX 08081162 comprising an added desired trait, the method comprising introducing a transgene conferring the desired trait into a plant of bean line RX 08081162, a sample of seed of said line RX 08081162 having been deposited under ATCC Accession Number PTA-12609.

21. A seed of the plant of claim 19.

22. A method of producing beans comprising:

(a) obtaining the plant of claim 2, wherein the plant has been cultivated to maturity, and (b) collecting beans from the plant.

* * * * *